United States Patent [19]

Phillips

[11] Patent Number: 4,955,856

[45] Date of Patent: Sep. 11, 1990

[54] METHOD AND APPARATUS FOR INSTALLING A VENTRICULAR ASSIST DEVICE CANNULAE

[76] Inventor: Steven J. Phillips, 5300 Woodland, Des Moines, Iowa 50312

[21] Appl. No.: 374,652

[22] Filed: Jun. 30, 1989

[51] Int. Cl.$^5$ .............................................. A61M 1/03
[52] U.S. Cl. ....................................... 600/16; 604/174; 623/3
[58] Field of Search ..................... 600/16, 17; 604/174, 604/175, 43; 623/3

[56] References Cited

U.S. PATENT DOCUMENTS

| | | | |
|---|---|---|---|
| 3,713,441 | 1/1973 | Thomas | 604/175 |
| 4,016,884 | 4/1977 | Kwan-Gett | 604/175 |
| 4,129,129 | 12/1978 | Amrine | 128/348 |
| 4,468,216 | 8/1984 | Muto | 604/19 |
| 4,583,968 | 4/1986 | Mahurkar | 604/43 |
| 4,596,548 | 6/1986 | DeVries et al. | 604/43 |
| 4,619,643 | 10/1986 | Bai | 604/43 |
| 4,645,492 | 2/1987 | Weeks | 604/174 |
| 4,662,355 | 5/1987 | Pieronne et al. | 623/3 |
| 4,682,978 | 7/1987 | Martin | 604/43 |
| 4,737,147 | 4/1988 | Ferrando et al. | 604/43 |

OTHER PUBLICATIONS

Color Photograph of a SYMBION ACUTE VENTRICULAR ASSIST DEVICE.
Black and White Photograph of a Symbion Acute Ventricular Assist Device.
Copy of pp. 708–711 of vol. XXXIV Trans Am Soc Artif Intern Organs, 1988–entitled Simplified Method of Hemofiltration in Ventricular Assist Device Patients.
Copy of pp. 445–449 of vol. XXXIV Trans Am Soc Artif Intern Organs, 1988–entitled State of the Art–Circulatory Support.
Copy of pp. 235–239 of vol. XXXI Trans Am Soc Artif Intern Organs, 1985 article entitled Surgical Approaches to Applying an LVAD in a "One Pump TAH" Configuration.

*Primary Examiner*—Francis Jaworski
*Assistant Examiner*—George Manuel
*Attorney, Agent, or Firm*—Henderson & Strum

[57] ABSTRACT

A method for installing a ventricular assist device cannula of a novel type including a blood drainage cannula tube having a first end and a second end and a blood inlet cannula tube having a first end and a second end with the tubes being attached together to form a sealed section having a convex outer periphery. The method includes making an opening in a heart, inserting the blood drainage cannula tube through the opening whereby the first end is disposed in a heart chamber and at the same time inserting the blood inlet cannula tube through the opening and also inserting it through the aortic valve so that the first end thereof is disposed in the aorta. At the convex surface, the ventricular assist device cannula is sutured to the heart to hold it in place and to prevent blood drainage therearound. The blood drainage cannula tube is attached to the inlet port of a pump and the second end of the blood inlet cannula tube is connected to the outlet end of the pump whereby this design and method of cannula requires only one opening into the heart instead of two.

3 Claims, 2 Drawing Sheets

METHOD AND APPARATUS FOR INSTALLING A VENTRICULAR ASSIST DEVICE CANNULAE

TECHNICAL FIELD

A ventricular assist device and a method of using it with left, right or bi-ventricular failure, and more particularly to such a device and method which requires making only one hole for each ventricular failure, instead of two as in conventional methods.

BACKGROUND ART

Ventricular assist devices (VAD) are gaining increased popularity for use in patients with left, right or bi-ventricular failure. Standard techniques require insertion of a cannula for drainage of the atrium or ventricle with insertion of a second cannula for re-infusion of blood into the aorta or pulmonary artery. This requires two cannulae for a single ventricular assist device and four cannulae for a bi-ventricular assist device. Physicians who have worked with ventricular assist device systems understand the space constraints and the potential kinking or twisting of these cannulae in the chest or at the skin insertion site. In addition, the theory is that the greater number of cannulae that are exteriorized, the greater the chance of transcutaneous contamination and infection.

DISCLOSURE OF THE INVENTION

The present invention relates to a cannula which contains two lumens fabricated for use in ventricular assist device cannulation. A small lumen cannula is mounted on a larger lumen cannula. The small diameter lumen cannula extends beyond the larger cannula by approximately 30 centimeters. This small diameter lumen cannula can be shortened to a desired length. The larger diameter lumen provides drainage into the ventricular assist device and the small lumen provides reflow from the ventricular assist device. The cannula is placed through a purse-string suture in the left or right ventricle.

The larger diameter lumen (drainage lumen) is disposed in the ventricle while the smaller lumen cannula passes through the aorta or pulmonic valve into the aorta or pulmonary artery. Thus, for left ventricular assist device use, the double lumen cannula is positioned as follows. The larger cannula is disposed within the left ventricle while the smaller cannulae passes through the left ventricle across the aortic valve into the aorta.

For right ventricular assist device insertion, the larger cannula is disposed in the right ventricle and the smaller cannulae passes through the right ventricle lumen across the pulmonic valve into the pulmonary artery. Exteriorization of these cannulas is basically in straight below the costal margins.

An object of the present invention is to provide an improved method and apparatus for installing ventricular assist device cannulae.

Another object of the present invention is to eliminate the need for making two holes in the heart to install a ventricular assist device cannula in either the right or left ventricle of a heart.

A further object of the present invention is to provide an apparatus having blood inlet and blood drainage cannulae tubes for use with the above mentioned method which can easily be sealed to the inner periphery of an opening in a heart with a standard purse string suture.

Other objects, advantages, and novel features of the present invention will become apparent from the following detailed description of the invention when considered in conjunction with the accompanying drawings.

BEST MODES FOR CARRYING OUT THE INVENTION

Figures 1, 2:
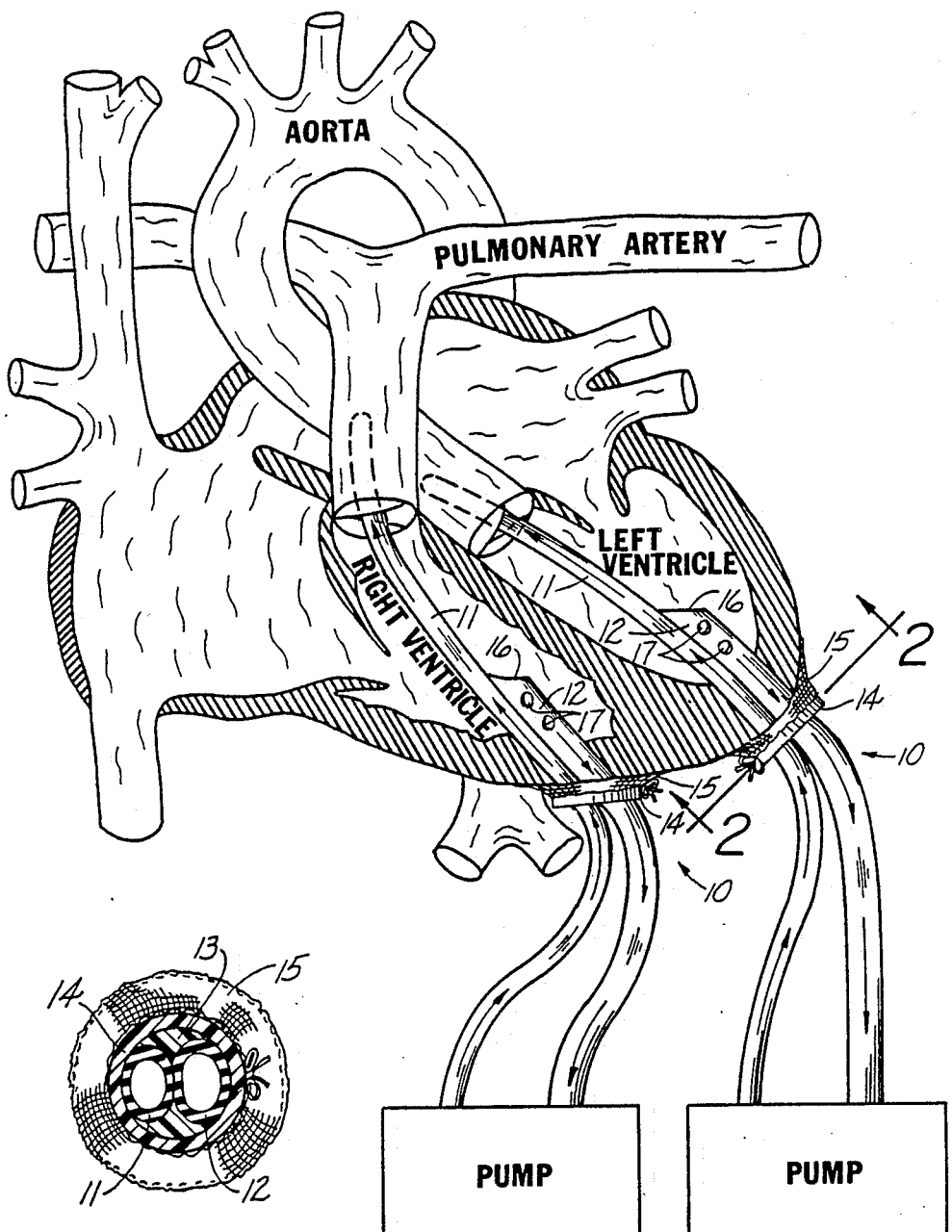
FIG. 1 is a cross-sectional view through a human heart and showing the placement of a ventricular assist device cannula in the left ventricle and another in the right ventricle thereof.
FIG. 2 is a cross-sectional view taken along line 2—2 of FIG. 1 to show how the two cannula tubes are joined together and sealed so that a easy purse string suture can be made therearound for an effective seal.

Referring now to the drawings wherein like reference numerals designate identical or corresponding parts throughout the several views, FIG. 1 shows a human heart having the apparatus of the present invention attached thereto. A ventricular assist device (10), shown in the present invention, has a small lumen inlet tube (11) attached to a larger blood drainage cannula tube (12) at the juncture shown in FIG. 2.

These tubes (11) and (12) are made of standard flexible plastic material and in one embodiment thereof, as shown in FIG. 2, a flexible plastic material is used to bond the two tubes (11) and (12) together and to fill in the openings around the joint between the two so as to form a convex surface (14). It is important that this convex surface (14) be present because if a concave surface (such as if the substance (13) were not used to fill in between the tubes at the juncture thereof) then it would be difficult to seal around a concave surface at (14) by the use of a standard purse string suture (15).

The small lumen cannula tube (11) extends beyond the larger cannula tube (12) by approximately 30 centimeters. This small lumen cannula (11) can be cut shorter to a desired length by the surgeon using it. The larger drainage lumen cannula (12) provides drainage to the ventricular assist device (10) and the small lumen cannula tube (11) provides reflow from the ventricular assist device (10). The device (10) is placed through an opening formed in the heart at either the left ventricle or right ventricle as shown in FIG. 1, or in both as shown in FIG. 1.

The larger drainage lumen cannula tube (12) has an open end (16) and additional flow openings (17) positioned in the ventricle while the smaller inlet lumen cannula tube (11) passes through the aortic valve, in the case of the left ventricle, or through the pulmonary artery, in the case of the right ventricle usage.

Therefore, for the left ventricular assist device usage, the double lumen cannula (10) is positioned by placing the blood drainage cannula tube (12), as shown in FIG. 1, in the left ventricle as shown, while the blood inlet cannula tube (11) is placed through the left ventricle and across the aortic valve so that the open end extends into the aorta.

For right side ventricular assist device insertion, an opening is made in the right ventricle in the position shown in FIG. 1 and the blood drainage cannula tube (12) is inserted therethrough to the position shown in FIG. 1, while the smaller blood inlet cannula tube (11) passes through the right ventricle lumen across the pulmonic valve and until the open end thereof is in the pulmonary artery. Of course, a purse string suture is then made around the convex portion (14) of the device (10) by a rayon annular collar (15), or the like. The suture is completed by sewing the rayon collar (15) to the heart itself. Exteriorization of these cannulas is basically straight below the costal margins. A left ventricular assist device will require only one cannula device (10) as shown and, likewise, a right ventricular device would require only one cannula as well. A bi-ventricular assist device will, of course, require two of the devices (10) such as shown in FIG. 1.

Figure 3:
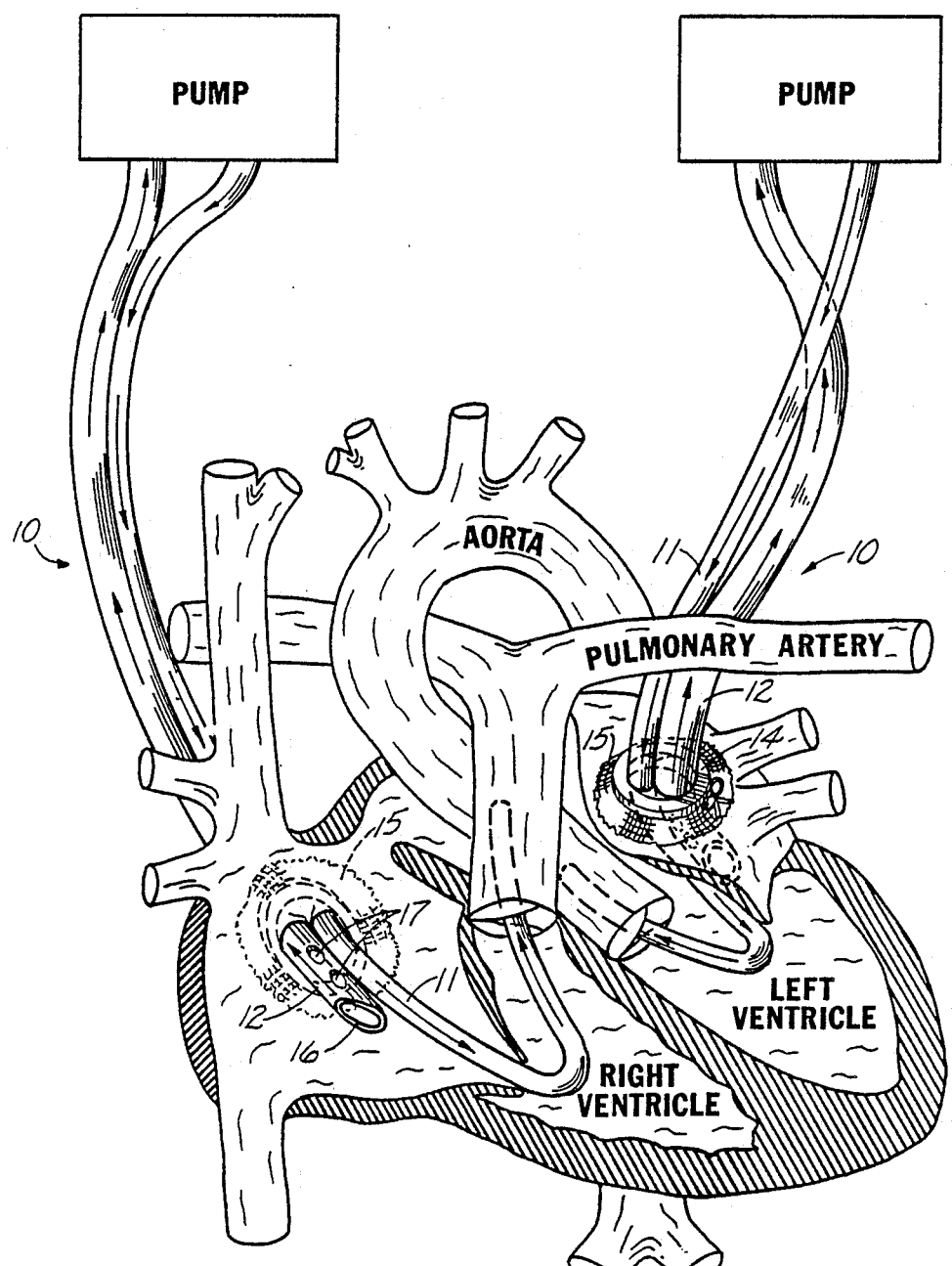
FIG. 3 is a cross-sectional view of the heart as shown in FIG. 1 but showing an alternate arrangement for installation of the apparatus of the present invention in the left and right sides of the heart.

It will be understood of course that the devices (10) do not need to be attached precisely in the position shown in FIG. 1. For example, FIG. 3 shows an alternate positioning of the devices (10) in the left and right sides of the heart.

Accordingly, it will be appreciated that the preferred embodiment disclosed herein does indeed accomplish the aforementioned objects. Obviously many modifications and variations of the present invention are possible in light of the above teachings. It is therefore to be understood that, within the scope of the appended claims, the invention may be practiced otherwise than as specifically described.

I claim:

1. A method of installing a ventricular assist device cannulae of a type including a blood drainage cannula tube having a first end and a second end and a blood inlet cannula tube having a first end and a second end, said method comprising:

making a single opening in a heart;
   inserting the blood drainage cannula tube through said single opening whereby said first end thereof is disposed in a heart chamber;
   inserting the blood inlet cannula tube through said opening and through the aortic valve so that said first end thereof is disposed in said aorta;
   suturing said blood drainage cannula tube and said blood inlet cannula tube to said opening for sealing said opening and holding said cannula tubes in place;
   attaching said second end of said blood drainage cannula tube to the inlet port of a pump; and,
   attaching said second end of said blood inlet cannula tube to the outlet port of said pump whereby this design of cannula only a single opening into the heart is needed instead of two.

2. A method of installing a ventricular assist device cannulae of a type including a blood drainage cannula tube having a first end and a second end and a blood inlet cannula tube having a first end and a second end, said method comprising:

making a single opening in a heart;
   inserting the blood drainage cannula tube through said single opening whereby the first end thereof is disposed in a heart chamber;
   inserting the blood inlet cannula tube through said single opening and through the pulmonic valve so that said first end thereof is disposed in said pulmonary artery;
   suturing said blood drainage cannula tube and said blood inlet cannula tube to said opening for sealing said opening and holding said cannula tubes in place;
   attaching said second end of said blood drainage cannula tube to the inlet port of a pump; and
   attaching said second end of said blood inlet cannula tube to the outlet port of said pump whereby with this design of cannula only a single opening into the heart is needed instead of two.

3. A ventricular assist cannula comprising:

a blood drainage cannula tube having a first end and a second end;
   a blood inlet cannula tube having a first and a second end;
   means for sealingly attaching an inermediate portion of the blood drainage cannula tube to an intermediate portion of the blood inlet cannula tube to form a convex outer surface;
   annular flexible suturing sleeve means extending around said convex outer surface being adapted and dimensioned for attachment to the interior periphery of a single opening in a heart; and
   suture means for sealingly attaching said annular flexible suturing sleeve means to said convex outer surface.

* * * * *